(12) United States Patent
Roehrl et al.

(10) Patent No.: US 7,794,442 B2
(45) Date of Patent: Sep. 14, 2010

(54) DISPOSABLE DIAPER

(75) Inventors: Wolfgang Roehrl, Herbrechtingen (DE); Matthias Bandorf, Schweinfurt (DE); Ruediger Kesselmeier, Herbrechtingen (DE)

(73) Assignee: Paul Hartmann AG, Heidenheim (DE)

( * ) Notice: Subject to any disclaimer, the term of this patent is extended or adjusted under 35 U.S.C. 154(b) by 698 days.

(21) Appl. No.: 11/665,849

(22) PCT Filed: Nov. 22, 2005

(86) PCT No.: PCT/EP2005/012472
§ 371 (c)(1),
(2), (4) Date: Apr. 20, 2007

(87) PCT Pub. No.: WO2006/056396
PCT Pub. Date: Jun. 1, 2006

(65) Prior Publication Data
US 2007/0293835 A1    Dec. 20, 2007

(30) Foreign Application Priority Data
Nov. 27, 2004    (EP) .................................. 04028211

(51) Int. Cl.
*A61F 13/15* (2006.01)
(52) U.S. Cl. .................... 604/387; 604/386; 604/385.03
(58) Field of Classification Search ............ 604/385.01, 604/385.03, 385.24, 386–394
See application file for complete search history.

(56) References Cited
U.S. PATENT DOCUMENTS

| | | | | |
|---|---|---|---|---|
| 4,964,860 | A * | 10/1990 | Gipson et al. ............... | 604/391 |
| 6,443,930 | B1 | 9/2002 | Silverstein | |
| 2001/0034512 | A1* | 10/2001 | Karlsson et al. ............. | 604/392 |
| 2002/0045881 | A1 | 4/2002 | Kusibojoska | |
| 2004/0236304 | A1 | 11/2004 | Coates | |
| 2005/0192555 | A1* | 9/2005 | Thomas ....................... | 604/402 |

FOREIGN PATENT DOCUMENTS

| WO | WO 01/43672   | 6/2001 |
| WO | WO 02/24134   | 3/2002 |
| WO | WO 2004/069122 | 8/2004 |

* cited by examiner

*Primary Examiner*—Michele Kidwell
(74) *Attorney, Agent, or Firm*—Paul Vincent

(57) ABSTRACT

A disposable diaper (29, in particular used in the event of incontinence, comprises a hip band (10). The hip band (10) comprises a first hip band section (10a) and second hip band section (10b). A least the second hip band section (10b) comprises a first closure means (26) provided with a side (261) which is oriented away from the body during use thereof and a side (262) which is oriented towards the body during use thereof, and at least the first hip band section (10a) comprises a second closure means (88). The side of the first closure means (262) which is oriented towards the body is attached in a detachable manner to the second closure means (88) in order to form a closed hip opening, and comprises a diaper main section (4) comprising a front area, a back area and a crotch area which is arranged there between, said diaper main section also comprises an absorption area (6) for fluids. The main part of the diaper (4) can be attached in a detachable manner to a fourth closure means (99) on the side of the hip band (10) oriented away from the body by means of at least one third, mechanical closure area (34) by means of the longitudinal end of the front region thereof or the rear area, and the third mechanical closure means (34) can be attached in a detachable manner to the side of the first closure means (261) which is oriented away from the body.

33 Claims, 9 Drawing Sheets

Fig 12

# DISPOSABLE DIAPER

This application is the national stage of PCT/EP2005/012472 filed on Nov. 22, 2005 and also claims Paris Convention priority of EP 04 028 211.3 filed on Nov. 27, 2004.

BACKGROUND OF THE INVENTION

The invention concerns a disposable diaper, in particular, for incontinent care, comprising a hip belt which forms a hip opening of the diaper which is closed in the peripheral direction, and which can be opened and closed on top of itself at least at one location using first and second closure elements, with a diaper main part having a front area, a rear area and an intermediate crotch area, and an absorption element for liquids, wherein the diaper main part can be detachably fixed, at the longitudinal end of its front area or rear area, to the hip belt via third closure elements, such that a user can pull the diaper main part from between the legs after application of the hip belt, and detachably fix the free longitudinal end of the diaper main part to the hip belt.

A disposable diaper of this type is disclosed e.g. in WO-01/00129-A1.

Disposable diapers of this type, which are also often called belt diapers, are advantageous in that the user initially puts the hip belt around the hips for applying the diaper, and usually closes it in the belly area. This is realized by fixing one hip belt section using first closure elements on the side, facing away from the body, of the other hip belt section to second closure elements thereof so that they overlap. In the meantime, the diaper main part of the disposable diaper, which is usually fastened in its rear area to the belt, hangs loosely downwards. After closing the hip belt, the user grasps the freely hanging end of the diaper main part and guides the diaper main part from behind through the legs in order to detachably fix the free longitudinal end of the diaper main part to the outside of the hip belt. Towards this end, the free longitudinal end has third closure elements which are usually designed as mechanical closure elements, in particular, as VELCRO fastener hooks, and fourth closure elements on the side of the hip belt facing away from the body, which are usually designed as a loop-forming fiber material, in particular as a nonwoven material. Clearly, the disposable diaper may also be applied in such a manner that, after application and closing of the hip belt, the diaper main part which is freely hanging downwards is guided from the front to the rear between the legs of a user and is detachably fixed with its rear area to the hip belt. There are also conventional disposable diapers with which the diaper main part can be completely detached from the hip belt, such that flexible handling of the disposable diaper is guaranteed, in particular, for users who need a great deal of care or who are immobile.

One disadvantage of the conventional belt diapers is the lack of flexibility for fixing the free longitudinal end of the diaper main part to the hip belt using the third and fourth closure elements. The conventional third mechanical closure elements are designed such that they can cooperate with the fourth closure elements, in particular with the entire outer side of the material forming the hip belt, in an adhering fashion in correspondence with their primary function. After fixing the hip belt sections to form a closed hip opening using the first and second closure elements, the first closure elements cover part of the fourth closure elements, since the first closure elements usually project past the side edge of the hip belt section. This part of the fourth closure elements can therefore no longer be used as a landing zone for the third, mechanical closure elements. This limits the possibilities of exactly fixing the free longitudinal end of the diaper main part to the hip belt using the third and fourth closure elements. This disadvantage is particularly unfavorable when the first and third closure elements adheringly cooperate with the entire outer side of the material forming the hip belt. In this case, the second and fourth closure elements coincide.

It is therefore the underlying purpose of the present invention to overcome the disadvantage of insufficient flexibility for perfectly fitting a belt diaper using third mechanical closure elements.

SUMMARY OF THE INVENTION

This object is achieved in accordance with the invention with a disposable diaper of the above-mentioned type in that the third mechanical closure elements can also be detachably fixed to the side of the first closure elements facing away from the body. The invention ensures that the third mechanical closure elements adhere not only to the fourth closure elements of the hip belt: the side of the first closure elements, facing away from the body, also adheres to the third mechanical closure elements. This adhering connection should be sufficiently large to ensure the primary function of the closure elements, i.e. secure retention of the diaper during use.

This adhering connection can be realized in any fashion, e.g. using adhesive. However, in an advantageous fashion, the side of the first closure elements facing away from the body, is formed, at least in sections, of a fiber material such as, in particular, a nonwoven material, preferably a card web or a spunbonded material, or a textile material.

In a further development of the invention, the first and/or third closure elements are elastic, at least in sections. This further increases the possibilities of adjusting the disposable diaper for perfect fit. The elastic section of the respective closure elements is advantageously formed from an elastic sheet or an elastic nonwoven material consisting of one or more layers, or an elastic nonwoven sheet laminate. An elastic sheet component may thereby e.g. be fixed in a stretched state to a nonwoven component which is not elastic per se, such that the formed nonwoven sheet laminate has elastic properties. For the first closure elements, the nonwoven component should preferably be disposed so that it faces away from the body, and should be designed so that the third closure elements can be fixed to it.

In order to ensure a sufficiently large surface for the adhering connection of the first and second closure elements, the first closure elements project past the side edge of the hip belt by at least 10 mm, in particular at least 20 mm, moreover in particular at least 30 mm and preferentially by at least 40 mm. The first closure elements extend in the longitudinal direction of the belt diaper by, in particular at least 15 mm, in particular at least 20 mm, in particular at least 25 mm, in particular at least 30 mm, and preferentially at least 35 mm. The present invention also permits selection of the size of the first closure element exclusively in accordance with optimum fulfillment of its primary function, i.e. sufficient adhering force for cooperation with the second closure elements. Even a very large first closure element does not limit the user's flexibility during subsequent fixation of the free longitudinal end of the diaper main part to the hip belt using third closure elements, since the third closure elements also adhere with sufficient strength to the side of the first closure elements facing away from the body, i.e. can ensure secure retention of the diaper during use.

In a further design of the inventive idea, the materials of the closure elements are matched, such that the adhering force as shearing force, (measured as described below), between the side of the first closure element facing away from the body, and the third closure element is smaller than the adhering force as shearing force between the side of the first closure element facing the body and the second closure element. This ensures that, during use of the diaper and under the action of a corresponding force, only the fixed end of the diaper main part will become detached from the hip belt in the worst case, while the hip belt itself remains closed, such that the belt diaper is not completely released from the body.

In a particularly advantageous embodiment of the present invention, the adhering force between the side of the first closure element facing the body and the second closure element is at least 5 N/25 mm, in particular at least 10 N/25 mm, moreover in particular at least 15 N/25 mm, moreover in particular at least 20 N/25 mm, moreover in particular at least 25 N/25 mm, moreover in particular at least 30 N/25 mm, moreover in particular at least 35 N/25 mm, moreover in particular at least 40 N/25 mm, moreover in particular at least 45 N/25 mm, and moreover at least 50 N/25 mm. The adhering force between the side of the first closure element facing the body, and the second closure element is advantageously less than 80 N/25 mm, in particular less than 70 N/25 mm.

The adhering force between the side of the first closure element facing away from the body, and the third closure element is advantageously at least 2 N/25 mm, in particular at least 3.5 N/25 mm, moreover in particular at least 5 N/25 mm, moreover in particular at least 10 N/25 mm, moreover in particular at least 15 N/25 mm, moreover in particular at least 20 N/25 mm, moreover in particular at least 25 N/25 mm, moreover in particular at least 30 N/25 mm, moreover in particular at least 35 N/25 mm, moreover in particular at least 40 N/25 mm, moreover in particular at least 45 N/25 mm, and moreover in particular at least 50 N/25 mm.

However, the adhering force between the side of the first closure element facing away from the body, and the third closure element is advantageously less than 70 N/25 mm, in particular less than 60 N/25 mm.

Figure 10:
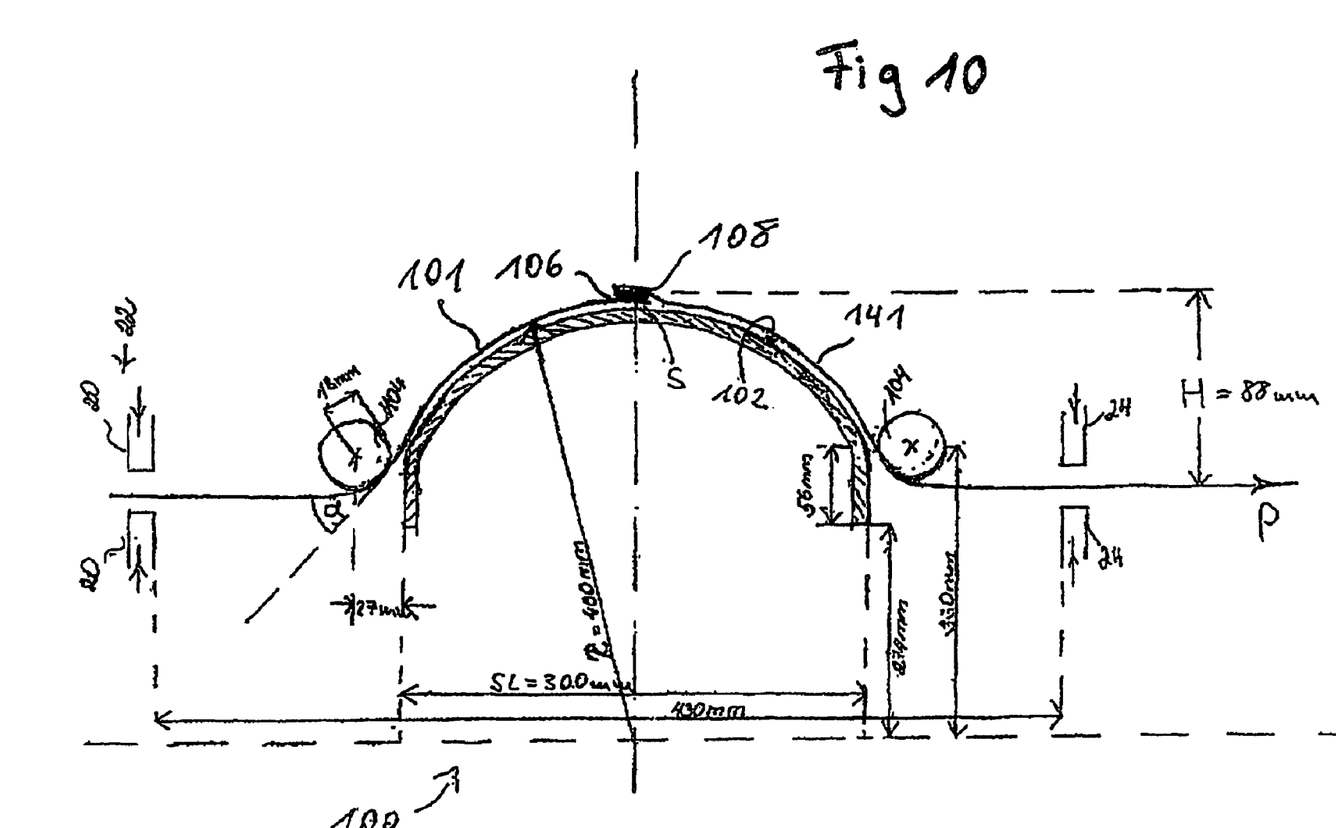
FIG. 10 shows a schematic view of the structure of a tension test with a device with curved surface.
Figures 11A, 11B:
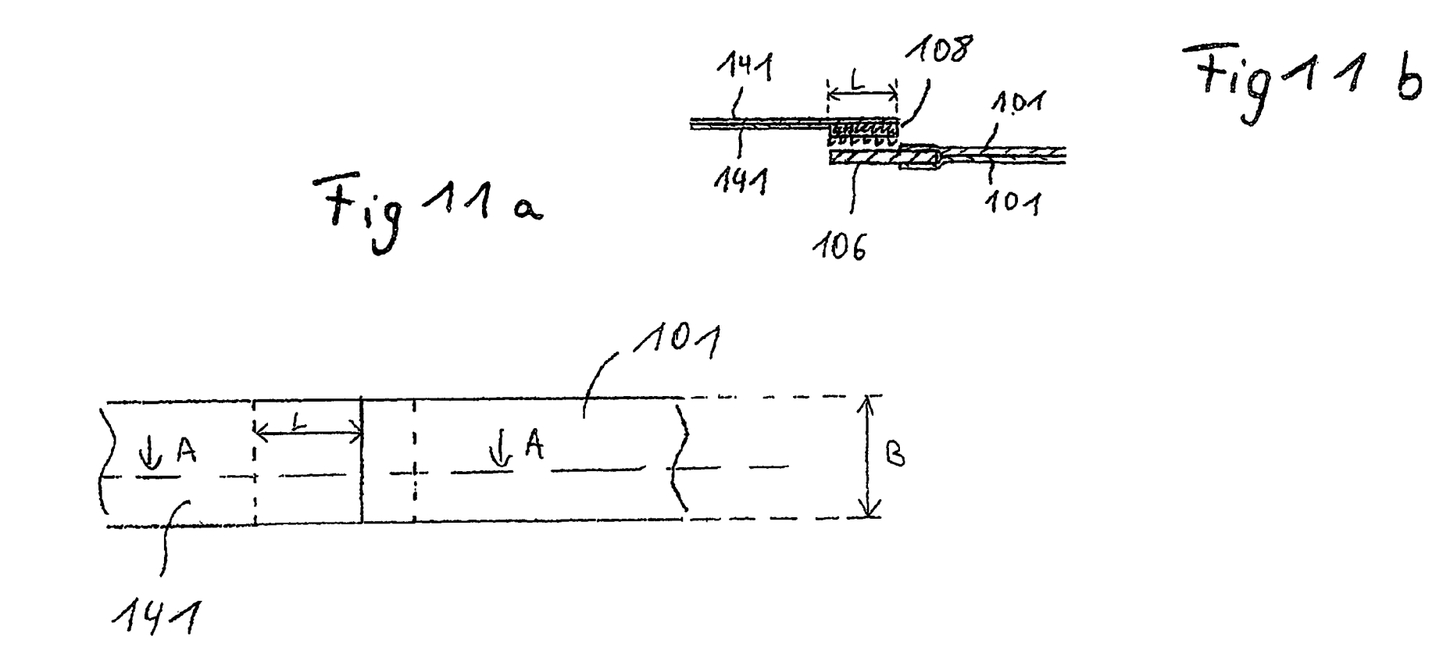
FIGS. 11a, 11b show schematic views of the sample.

A test method is described below for determining the adhering forces at shearing stress. The test method may be performed by a tension testing machine of the type Z010/TN 2S, measuring load 100 N, available from the company Zwick GmbH & Co KG, Ulm, Germany, which has a 60 mm clamping jaw width for clamping the sample. For performing the test method, the tested closing system with a first e.g. loop-forming component 106 and a second e.g. hook-forming component 108 which adheres thereto, is disposed (FIGS. 10-11) over a curved surface which simulates the curvature of the belly area of a user (FIG. 10). The closure element is connected to the clamping jaws of the tension testing machine by a flexible substrate 141, 101, e.g. an adhesive tape, which is adhesive on one side, of a preferred width of 25 mm, available under the trade name STA 306 from the company 3M Deutschland GmbH in Neuss. The adhesive tape is made of polypropylene and its surface is coated with a urethane-modified silicon polymer. The surface density of the adhesive application is 23 g/m$^2$. The sample disposed over the curved surface and consisting of planar sections of the closure element 106, 108, which are disposed on top of each other in an adhesive fashion, is tensioned by the tension testing machine to exert shearing stress onto the adhering planar sections.

Preparation of the Sample:

The mechanical closure elements to be used are conditioned for 24 h at 23° C. and 50% relative air humidity. Samples 106, 108 of a size of 25×30 mm (width B×length L) are punched out of the closure element materials and disposed or fixed like a sandwich between the ends of two one-sided adhesive tapes 101, 141 of a width of 25 mm, which are glued against each other, such that the closure side of the respective closure element material to be tested overlaps by 25×20 mm (width B×length L) (see FIGS. 11*a*, 11*b*). When hook-forming closure elements are to be tested, as in the case of FIGS. 11*a*, 11*b*, it is proposed to punch out the hook-forming component of the closure element 108 having dimensions of 25×20 mm, and fix it through two one-sided adhesive tapes 101 which are glued to each other at their adhesive sides, such that the upper adhesive tape overlaps the rear side of the flat section, and the lower adhesive tape is flush with the flat section (FIG. 11*b*).

The sections of the closure element materials prepared in this fashion are subsequently disposed on top of each other over their full surfaces (FIGS. 11*a*, 11*b*). When the closure elements of the closure element materials have a preferred direction, they are oriented as during use of the diaper.

The planar sections disposed on top of each other are connected to each other by rolling four times using a roller which is 50 mm wide and has a diameter of 100 mm with smooth surface and a weight of 5 kg. The rolling speed is 20 to 100 mm/sec.

Test Method

One end of the closure element materials, sized as described above, is centered and clamped in the lower clamping jaw of the tension testing machine, and the opposite end of the closure element material, sized as described above, is clamped in a centered position into the movable upper clamping jaw of the tension testing machine.

Figure 12:
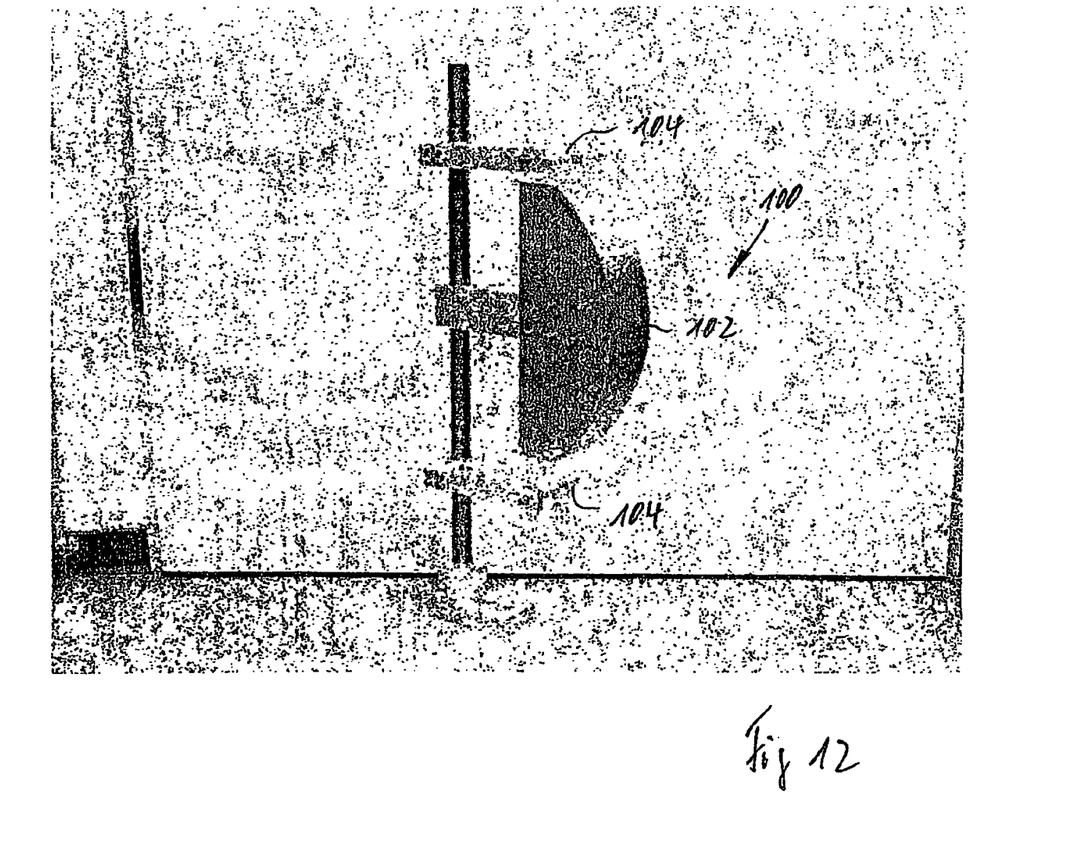
FIG. 12 shows a perspective view of the device of FIG. 10.

The clamped sample is disposed over the device 100 shown in FIGS. 10, 12, which simulates the belly or hip area of a user. This device 100 is shown in perspective view in FIG. 12. It shows a smoothly curved surface 102 of polished steel with a roughness height of 5 to 25 µm and with a radius of curvature R of 400 mm (at least in sections) and with a chord length SL of 300 mm. Deflection rollers 104 are moreover provided above and below the curved surface 102, having a diameter of 18 mm, which deflect the sample disposed on the curved surface, in a vertical direction by H=88 mm, where it is connected to clamps 20, 24 of the tension testing device (not shown). The sample is deflected through an angle α of 60°. This keeps the withdrawal angle substantially tangential to the curved surface and also constant. The planar sections 106, 108 disposed on top of each other of the components of the closure element are positioned relative to the curved surface 102, such that the upper component comes to rest in the center in the vertex S of the curved surface 102.

The movable clamp 24 to which the upper component is connected, is then moved with the test speed (as stated below) in the direction of arrow P and the tensile force between the clamps is thereby determined. The test parameters are:

| | |
|---|---|
| Test speed: | 300 mm/min |
| Clamping length of the sample | 430 mm (see FIG. 4) |
| Measuring path: | distance until detachment of the closure element components n |
| Pre-force: | 0.2 N |
| Test number: | n ≧ 6 |

In the evaluation, the maximum force determined before the closure elements become detached, rounded to two decimal points in N (Newton), is noted and stated in the form of an average value of the n measurements and the standard deviation as well as a minimum value and a maximum value.

In a further development of the invention, the hip belt is formed by a one-piece material section which is joined to the diaper main part.

A material section which extends continuously in one piece in the transverse direction of the hip peripheral direction is advantageously joined to the diaper main part to form the hip belt. Due to the flat joint, the tensile forces are not introduced into the diaper main part but can be completely accepted by the tear-resistant belt material. This increases the flexibility for selecting the chassis materials forming the main part and moreover reduces the requirements for the stability of the joint between the belt and the main part. The material section forming the belt can be obtained as one single longitudinal section of a flat material sheet supplied in the machine direction.

In an advantageous embodiment of the invention, the hip belt is folded on top of itself on both sides of a longitudinal central axis by at least one, in particular, at least two, and preferentially at least three folding lines that extend in the longitudinal direction of the diaper.

In a further design of the inventive idea, the hip belt is advantageously detachably fixed in the configuration which is folded on two sides, such that it is not inadvertently unfolded or opened within the fast running production machine. Folding and detachable fixing of the hip belt in the folded configuration advantageously permits joining of the very long hip belt to the main part in the production machine.

In a further development of this inventive idea, the detachable fixing is advantageously formed by joining locations or joining areas between the partial sections, folded on top of each other, of the material section forming the hip belt. The folded configuration could also be detachably fixed by other holding means, e.g. a detachable tape section.

The above-mentioned fixing, which can be released in one step, of the partial sections, which are folded on top of each other, of the material section joined to the main part and forming the hip belt, can e.g. be obtained through cold pressing or pressing using temperature (thermo welding), through needling, in particular hot needling or ultrasound welding or laser welding or similar joining methods having the same effect.

Detachable fixing of the material section partial sections, which are folded on top of themselves, to each other and possibly also to the main part is advantageously developed through several substantially point-shaped joining locations. A point-shaped joining location of the above-mentioned type means that the joining location has a surface (as projected onto the X-Y plane of the main part) of less than 5 mm$^2$, in particular less than 2 mm$^2$ and preferentially less than 1 mm$^2$. The joining locations need not be strictly point-shaped or circular. Shapes other than point-shaped or circular, such as e.g. triangular, rectangular, polygonal or oval shapes are also feasible and advantageous. The detachable fixing between the material section partial sections which are folded on top of each other is advantageously formed through preferably point-shaped joining locations generated by heat or ultrasound.

In accordance with a further preferred embodiment of the inventive belt diaper, the one-piece material section of folded configuration projects with one grasping area at its free end past a longitudinal side edge of the diaper main part in the transverse direction by, in particular at least 5 mm, in particular at least 20 mm, in particular at least 30 mm, and preferentially at least 40 m, and moreover at least 50 mm, and preferentially at least 60 mm. The grasping area can be formed, in particular, by the respective free end of the hip belt.

Before the one-piece material section is unfolded, the grasping areas preferably face to the outside in a transverse direction, i.e. face away from each other and from a longitudinal central axis of the diaper main part disposed on a flat support, such that it can be easily grasped by the left hand of the user from the left-hand side and by the right hand from the right-hand side. The belt diaper is particularly advantageous for persons requiring a great deal of care. The belt diaper is e.g. often applied to persons needing care while lying on their sides. The material section which laterally projects past the main part must thereby be guided from beneath the patient. This process of guiding beneath the patient is substantially simplified by the detachably fixed, folded material section that forms the belt.

The material section forming the hip belt extends in the transverse direction in the unfolded state past the longitudinal edge of the main part by advantageously at least 200 mm, in particular at least 300 mm, in particular at least 400 mm, in particular at least 500 mm, in particular at least 600 mm and preferentially at least 700 mm.

It extends in the longitudinal direction by preferably 30 to 150 mm, in particular 40 to 130 mm, in particular 50 to 125 mm, in particular 60 to 120 mm, in particular 70 to 115 and moreover in particular 75 to 110 mm.

The material section forming the hip belt is advantageously undetachably fixed, in particular, to an outer side of the main part. It may be joined in any fashion. The preferably one-piece material section may advantageously be joined to the diaper main part by glue which is applied only in some areas. With particular advantage, the glue does not extend to the edge of the mutually abutting flat extension of the material section and the main part, such that a peripheral edge area of this composite remains free from glue. The glue is thereby advantageously prevented from being forced through between the layers and to the outside during lamination.

The preferably one-piece material section which is joined to the main part and forms at least sections of the hip belt is advantageously formed from a nonwoven material, in particular and advantageously through spunbond materials (S) or spunbond-meltblown materials (SM) or meltblown layers (SMS) provided on both sides with spunbond materials, or also carded and/or water needled nonwoven materials. The hip belt is thereby produced to be skin-friendly and have a large surface which serves as a landing surface for the first and third closure elements, i.e. a large-surface area which is provided as the second and simultaneously also fourth closure element for an adhering connection to the side of the first closure elements facing the body and the third closure element. Nonwoven laminates, i.e. in particular, two-layered, three-layered or multi-layered combinations of the above-mentioned nonwoven materials may also be used.

The individual layers may be connected by conventional and familiar methods, e.g. through thermal joining methods such as welding, in particular, laser welding, hotmelt, air-through, hot calender or ultrasound embossing, even cold embossing, needling, sewing or gluing of nonwoven materials is feasible. Connection to textile fabrics, knitted materials, i.e. with materials having a textile bond in the largest sense, is also feasible. Films of thermoplastic and, in particular, elastic materials can also be used, i.e. also as multi-layer film laminates. Nonwoven/sheet laminates may also advantageously be used, which comprise at least one film layer and at least one nonwoven layer or at least one layer of a textile material. Film layers are used in particular to realize elastic areas of the hip belt. The layers are in turn connected by the above-mentioned methods.

A loop-forming nonwoven material has turned out to be a particularly preferred material for at least sections of the hip belt, whose first upper side disposed to face away from the body during use comprises first larger nonbonded areas which are spaced apart from each other and disposed like islands, wherein these first larger nonbonded areas are delimited by bonded contours and are surrounded outside of the limitation by two smaller nonbonded areas and are separated from each other through these second smaller nonbonded areas.

The larger non-bonded areas are primarily available for forming a mechanically acting closing function. They are delimited or defined by a bonded contour which may be formed, in particular, through linear embossing, in particular thermal embossing, produced in particular through ultrasound welding or calendar embossing, wherein these embossing lines may be continuous or interrupted, in particular, dashed or dash-dotted lines. Further smaller non-bonded areas or fields are provided outside of this bonded contour between these first non-bonded island-type areas, which separate the first larger non-bonded areas from each other. The island-type larger areas are thereby disposed sufficiently proximate to each other, or the second smaller non-bonded areas surround bonded partial areas in such a manner that a maximum circular surface which can be inscribed in the first larger non-bonded areas cannot fit within the second non-bonded areas.

The nonwoven material provides an overall and individually projecting and sufficiently large anchoring area for the hook-forming component of the mechanical closure element in the first larger non-bonded island-type areas. The further second non-bonded areas between the island-type first non-bonded areas facilitate as continuous a mechanical connection as possible. An equally sufficient solidification of the loop-forming nonwoven material is obtained by the bonded contours which delimit the first non-bonded areas, and optionally supported by further bonded partial areas which, in turn, are surrounded by the second non-bonded areas and disposed between the first larger areas.

As mentioned above, the second smaller non-bonded areas advantageously have or, in particular, surround bonded partial areas to effect good solidity and proper embedding of the fibers of the nonwoven material. These partial areas which may also be formed by embossing, in particular thermal embossing, may have any shape, wherein relatively short, narrow segments have proven to be advantageous for the partial areas, having a longitudinal extension of approximately two to ten times (preferably two to eight times) their width.

Each straight connecting line advantageously extends between the first larger non-bonded island-type areas through a bonded contour or a bonded partial area which is disposed between the first larger areas in order to enhance embedding of the fibers into the nonwoven material.

The bonded contours advantageously have embossing lines or embossing line sections of a width of 0.2 to 1 mm, preferably 0.2 to 0.8 mm and moreover preferably 0.3 to 0.6 mm. They advantageously have a depth of 0.4 to 1.5 mm, preferably 0.4 to 0.9 mm, preferentially 0.4 to 0.8 mm and moreover preferentially 0.5 to 0.7 mm.

The first larger non-bonded island-type areas advantageously have a dimension, in particular, a diameter of a circle inscribed in the area of 2 to 15 mm, preferably 3 to 10 mm, preferentially 3 to 8 mm and with particular preference 4 to 7 mm.

The first larger non-bonded island-type areas advantageously have a surface portion of 5 to 75%, in particular 5 to 60%, in particular 10 to 50%, in particular 10 to 45%, in particular 15 to 45%, in particular 20 to 40%, and preferentially 30 to 40% of the overall surface of the first upper side. In accordance with the invention, it has turned out that the first larger non-bonded island-type areas may cover a relatively moderate portion of the overall surface, since the closing function is additionally supported by the smaller non-bonded areas or fields between the first larger non-bonded areas.

The shape of the first larger non-bonded island-type areas is not necessarily predetermined. Advantageously, they have a circular, oval, triangular or polygonal, preferably hexagonal or octagonal shape. These preferred structures provide an extensive anchoring area for the hook-forming component of the closure element. It turns out that the closing function is particularly effective through relatively large island-type areas having dimensions which are preferably the same in all directions, as is the case with a circle or regular polygon, in particular, hexagon.

In one particularly suitable arrangement of the first island-type areas, these areas have a mutual separation from each other of at least 1 mm, preferably at least 1.5 mm, in particular at least 2 mm and preferentially at least 2.5 mm and with particular preference at least 3 mm. However, they preferably have a maximum separation of at most 10 mm, in particular, at most 5 mm.

One can obtain good and sufficient stability of the nonwoven material, i.e. good embedding of the fibers and thereby great solidity of the nonwoven material when the overall surface portion of bonded areas is preferably 10 to 60%, preferably 15 to 40%, furthermore preferably 15 to 30%, in particular 15 to 25% and preferentially 19 to 22% of the overall area of the first surface. In this connection, bonded areas mean bonded contours which delimit the first island-type areas and also optionally additional bonded partial areas between the first island-type areas.

The nonwoven material, which forms at least sections of the hip belt, may preferably comprise a spunbonded material or a card web or a meltblown nonwoven or a water-needled nonwoven material. It may also advantageously be a nonwoven laminate which consists of several nonwoven layers. In accordance with a preferred embodiment of the invention, the material comprises a spunbonded material and a card web which are connected to each other. In this case, the card web advantageously forms the first upper side which constitutes a landing zone for a hook-forming component of a mechanical closure element.

When the nonwoven material consists of several nonwoven layers, i.e. is a nonwoven laminate, these layers are advantageously connected to each other through applying the bonded contours delimiting the first larger non-bonded island-type areas. This may be realized e.g. by thermo embossing, in particular, by calendar embossing or ultrasound welding. When the nonwoven material is formed as a nonwoven laminate, a nonwoven layer facing away from the first upper side may be solidified by a further bonding pattern generated, in particular, through thermo embossing, in order to increase the overall solidity. This further nonwoven layer thus does not form the landing zone for a hook-forming component of the closure element but is provided on the side facing away. The bonding pattern is preferably mounted during previous production of the further nonwoven layer to pre-solidify it.

The surface density of an inventive non-woven material is preferably 15 to 120 $g/m^2$, in particular 20 to 90 $g/m^2$, in particular 30 to 80 $g/m^2$, in particular 40 to 70 $g/m^2$, and preferentially 50 to 65 $g/m^2$.

The surface density of the nonwoven layer which forms the first upper side and has the first nonbonded island-type areas, the bonded contours and the second non-bonded areas is preferably 10 to 60 g/m², in particular 10 to 40 g/m², in particular 15 to 35 g/m², and moreover in particular 20 to 35 g/m².

The above-mentioned surface densities in connection with the claimed design of the first upper side produce nonwoven materials which do not only ensure good closing function in cooperation with a hook-forming component of a closure element but also have good mechanical properties, in particular, in view of comfortable flexibility, while, however, also assuming a supporting function.

In view of the design of the nonwoven material, the nonwoven layer which forms the first upper side advantageously and suitably has fibers of a thickness of 1 to 10 dtex, preferably 2 to 8 dtex and preferably 3 to 6 dtex or consists of such fibers. In another advantageous fashion, the nonwoven layer which forms the first upper side comprises hydrophilic fibers or consists of hydrophilic fibers.

When the nonwoven material consists of several nonwoven layers, it may comprise one nonwoven layer as a carrier which has a surface density of 10 to 100 g/m², preferably 15 to 60 g/m², and moreover preferably 30 to 40 g/m². This carrier layer faces away from the first upper side. It advantageously comprises fibers of a thickness of 1 to 6 dtex, preferably 1 to 4 dtex and moreover preferably 2 to 4 dtex.

In a particularly advantageous further development of the invention, the nonwoven material is breathable, i.e. permeable to water and/or air. This improves the comfort of wear.

As is mentioned above, the nonwoven material advantageously has a stiffness of <0.80 N in particular <0.60 N, in particular <0.40 N, in particular <0.30 N, in particular <0.25 N, in particular <0.2 N, in particular <0.18 N, and moreover in particular <0.16 N, however at least 0.05 N. This stiffness is determined in accordance with the test method described in EP 0 699 066 B1 of the modified version of the test ASTM D 4032-82 CIRCULAR BEND, the disclosure of which and the relevant content of EP 0 699 066 B1 are hereby explicitly incorporated by reference. In addition thereto, this test method is further specified, such that in the test arrangement the first upper side of the nonwoven laminate is disposed at the bottom, i.e. forms that surface which faces away from the punch of the test apparatus.

Further features, details and advantages of the invention can be extracted from the enclosed claims, the drawing, and the following description of a preferred embodiment of the inventive diaper.

BRIEF DESCRIPTION OF THE DRAWING

FIG. 6 shows a schematic sectional view of the nonwoven material of FIG. 7a;

FIG. 7b shows a sectional view (detail) of FIG. 7a;

FIG. 9 shows a schematic sectional view with sectional plane A-A of the belt diaper of FIG. 8 with a first fold of the hip belt;

DESCRIPTION OF THE PREFERRED EMBODIMENT

Figure 1:
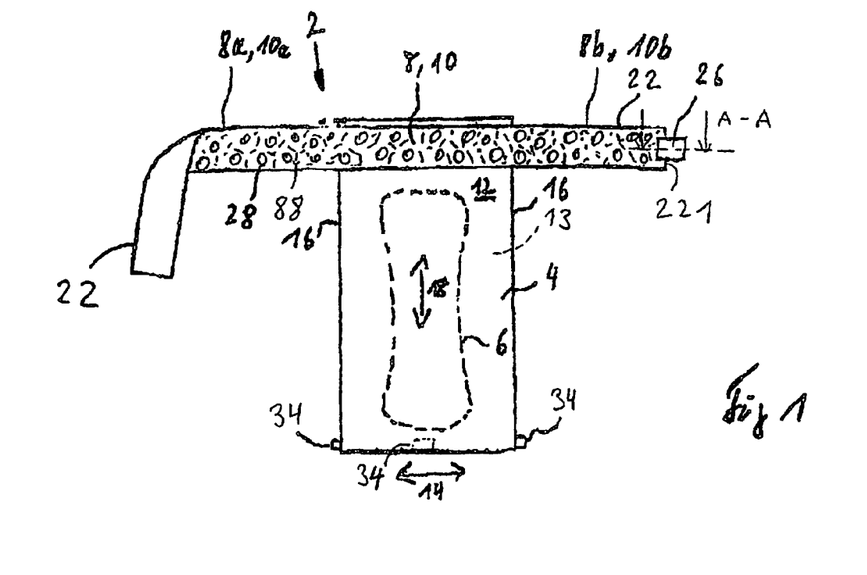
FIG. 1 shows a schematic view of an inventive belt diaper with open hip belt.

FIG. 1 schematically shows a disposable belt diaper 2 with a main part 4 and an indicated absorption element 6. A one-piece material section 8 is joined to the main part 4, which forms a hip belt 10 of the hip diaper. FIG. 1 shows the belt in the unfolded state. The one-piece material section 8 is undetachably joined to an outer side 12 of the main part 4. It extends in the transverse direction 14 of the belt diaper 2 via lateral longitudinal edges 16 in the unfolded state, through at least 300 mm, in particular at least 400 mm, in particular at least 500 mm, in particular at least 600 mm, in particular at least 700 mm in each case. In FIG. 1, the first material section 8a is considerably longer than the second material section 8b, i.e. the extension of the first hip belt section 10a in the unfolded state in the transverse direction 14 beyond the longitudinal edge 16 of the main part 4 is larger by preferably 100 mm, preferably 200 mm, and preferentially 300 mm than that of the second hip belt section 10b.

The first and second material sections may also have the same length.

Figure 2:
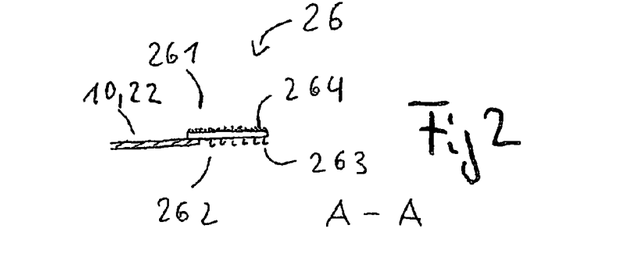
FIG. 2 shows a schematic sectional view of the first closure element with a sectional plane A-A of the belt diaper of FIG. 1.

A first closure element 26 is also provided at the end of the second hip belt section 10b, having the shape of a tab 26 with mechanical closure elements, which projects past the side edge 221 of the second hip belt section 10b, preferably by at least 10 mm, in particular by at least 20 mm, in particular by at least 25 mm. FIG. 2 shows that the first closure element 26 has a side 262 facing the body and a side 261 facing away from the body. The side 262 facing the body comprises mechanical closure elements, i.e. VELCRO fastener hooks 263 which adhesively cooperate with counter closure elements, i.e. second closure elements 88 on the first hip belt section 10a, in particular with its overall outer surface in a detachable adhering fashion, when the hip belt 10 is closed to form a hip opening which is closed in the peripheral hip direction.

Figure 4:
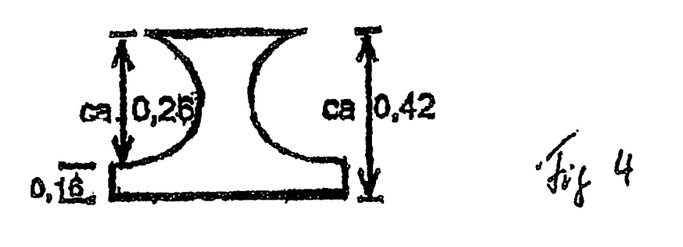
FIGS. 4 and 5 show views of a hook-forming component of a closure element.
Figure 5:
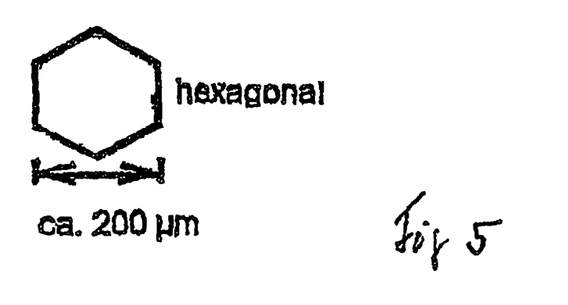

The side 261 facing away from the body comprises a nonwoven material 264 which cooperates in an adhering fashion with the mechanical closure elements 34 comprising the VELCRO fastener hooks 341 as is described in detail below. The closure elements 34 are formed in the present case by the material "Microplast" 42-288-HX200-PP3 by the company G. Binder GmbH & Co. KG Textil- and Kunststofftechnik, Holzgerlingen. FIGS. 4 and 5 show illustrations of the form of the hook-forming component. The hooks have a mushroom shape with approximately hexagonal surface of the head. There are approximately 288 such mushroom shaped projections per cm². The material consists of polypropylene and has a thickness of approximately 0.42 mm. The height of the mushroom shaped elevations relative to the ground of the material is approximately 0.26 mm. The separation of the edges of the heads is approximately 200 µm.

Figure 3:
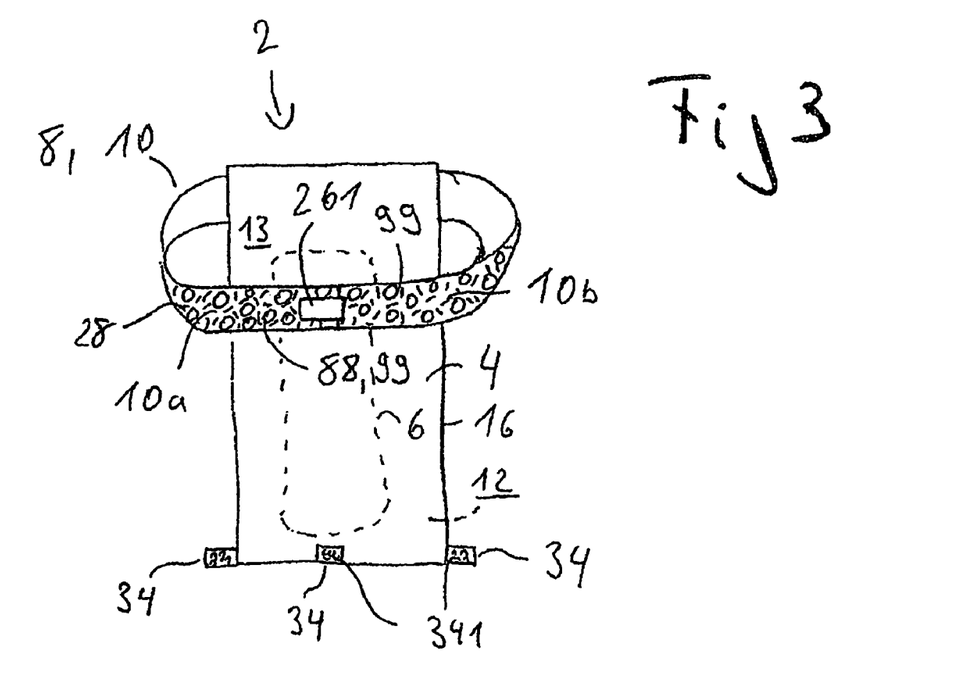
FIG. 3 shows a schematic view of an inventive belt diaper in accordance with FIG. 1 with closed hip belt.

FIG. 3 shows a view of the inner side 13 of the belt diaper 2 after fixing the first hip belt section 10b in an overlapping configuration to the second closure elements 88 of the first hip belt section to form the closed hip opening.

For final application of the belt diaper, 2 the main part 4 must be grasped from between the legs of a user and be detachably fixed to the outer side of the hip belt 10 through further mechanical closure elements, in particular, tabs 34 of the main part 4, having VELCRO fastener hooks 341. In accordance with the invention, this is effected not only by the fourth closure elements 99 on the outer side of both hip belt sections, but also by the side of the first closure element 26, facing away from the body, which is formed from a nonwoven material 264.

In the present case, the first closure elements 26 schematically shown in FIG. 2 are formed from an elastic VELCRO fastener diaper tape available from the company Köster GmbH & Co KG, in Altendorf, Germany, under the name CP2 EM 67 precut HC. The outer side of this tape, i.e. the side of the closure element 26 facing away from the body is completely covered by the nonwoven material 264. The nonwoven material 264 consists of a PP spunbonded material with thermally embossed diamond-shaped points whose outer side has a directly extruded film of a PP/PE polymer in order to roll up the VELCRO fastener diaper tape, which has an adhesive on the lower side for fixing to the side edge 221 of the second hip belt section 10b, in an endless fashion on itself during manufacture thereof without further separating materials such as release papers and to easily unwind it for application to the diaper. The surface density of the nonwoven material coated with the PP/PE polymer is 75 g/m$^2$.

The shearing force determined in accordance with the above-described test method between the side 261 facing away from the body of the first closure element 26 and the third closure elements 34 is 7.97 N/25 mm.

This force is sufficient to ensure reliable closure of the diaper during use under normal wear conditions.

The belt diaper can thereby be adjusted to different anatomies or sizes in a very flexible fashion.

In the illustrated case of a preferred embodiment, the entire outer side, i.e. the side of the hip belt 10 facing away from the body, has a loop-forming nonwoven material which also forms the second closure elements 88 and the fourth closure elements 99. This loop-forming nonwoven material is indicated with reference numeral 28.

Figure 6:
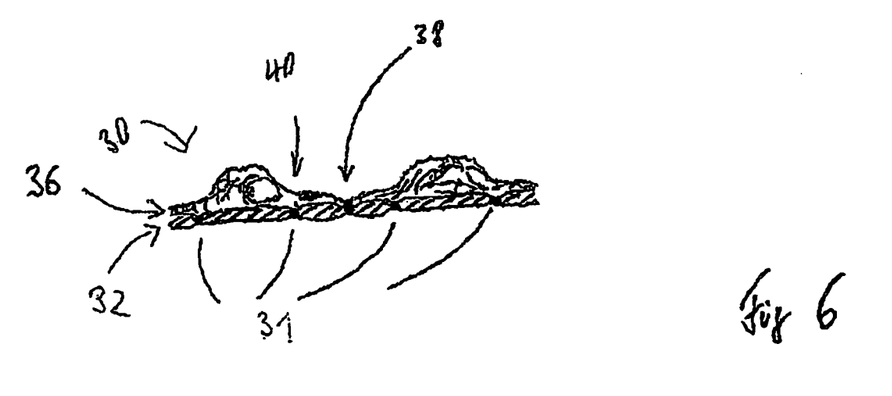
Figure 7A:
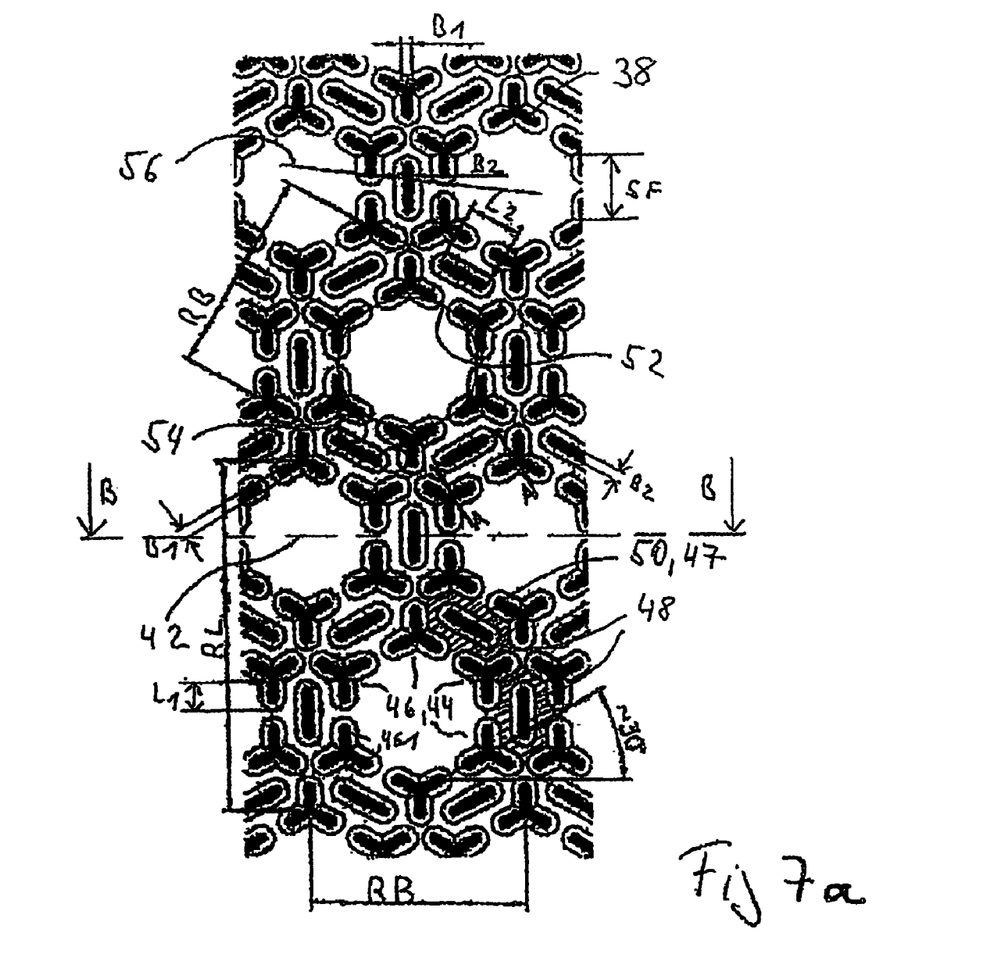
FIG. 7a shows a top view of the "unwound" surface of an engraving roller for embossing a nonwoven material, and also a schematic view of the first upper side of the nonwoven material forming the outer side of the hip belt.

The nonwoven material 28 consists of a nonwoven laminate 30 which is shown in a schematic sectional view in FIG. 6. The section thereby extends along a line B-B shown in FIG. 7a. It has a polypropylene spunbonded layer 32 consisting of fibers of a fiber thickness of 2.2 dtex with a surface density of 30 g/m$^2$ as a carrier, which is presolidified by oval bonding points 34 of a surface density of 48.37 points/cm$^2$ (thermal embossing points), wherein the dimensions of the semi-axes of the oval bonding points are 0.85 mm and 0.59 mm in each case, and the pressing surface of the oval bonding points is accordingly 0.394 mm$^2$ and the portion of the bonding points of the overall surface is thus 19.0%. The depth of the bonding points is 0.80 mm. A card web layer 36 is joined to this spunbonded layer 32 through hot calendar embossing. In the case shown, the card web consists of hydrophilized polypropylene fibers of a thickness of 4.4 dtex and a fiber length of 40 mm. FIG. 7a shows a view of the "unwound" surface of a calendaring roller which corresponds to an embossing pattern 38 disposed onto the first upper side 40 of the card web layer 36 through hot calendaring. FIG. 7a also schematically shows a view of the first upper side 40 of the nonwoven laminate 30.

First larger nonbonded areas 42 are formed on the first upper side 40 of the nonwoven laminate 30 through applying an embossing pattern 38, which are limited by a thermally bonded contour 44 of interrupted first segments 46. In the present case, these first segments 46 have a regular trilobal shape when viewed from above. The arms 461 of these first segments 46 have a length L1 of 1.04 mm and a width B1 of 0.47 mm. The limited first nonbonded areas are hexagonal and are disposed at mutual separations like islands on the first upper side 40. Second nonbonded areas 48 are located between the first areas 42, which are smaller than the first nonbonded areas 42. These second nonbonded areas, in turn, surround bonded partial areas 50 which are formed like bars by second segments 47. These second segments 47 have a length L2 of 2.07 mm and a width B2 of 0.47 mm. The embossing depth of the first and second segments is 0.59 mm in each case. In the example shown, the sides of the hexagon of the first non-bonded island-type areas have dimensions SF of 2.9 mm. Their separation is approximately 2.6 mm.

In particular, it is not possible to dispose a maximum size circle 52 inscribed in the first larger areas 42, having a diameter of 4.8 mm in the present case, within the second, nonbonded smaller areas 48. The maximum size circles 54 are indicated therein.

The pattern repeat (RB) of the embossing pattern 38 is 8 mm, the pattern repeat length RL is 13.86 mm.

The overall surface portion of bonded areas 44, 50 is 20.7%. The surface portion of the first larger nonbonded island-type areas (42) is approximately 35.7%, wherein the size of the surface of the inscribed circle 52 is used to determine the surface of a first nonbonded island-type area.

The shearing force determined in accordance with the above-described test method of this nonwoven material is 51.00 N/25 mm, wherein the material "Microplast" 42-288-HX200-PP3 by the company G. Binder GmbH & Co. KG Textil- and Kunststofftechnik, Holzgerlingen, was used as the VELCRO fastener hook component.

The rigidity of the nonwoven material determined in accordance with the test method disclosed in EP0699066B1 is 0.13 N, wherein in the test arrangement the spunbonded side is at the top, i.e. forms the surface which faces the punch of the test apparatus.

In a further embodiment of the present invention, only the surface density of the spunbonded material was increased to 45 g/m$^2$ and the embossing pattern 38 connecting the nonwoven materials was modified:

Length L1 of the arms 461 of the first segments 46: 1.0 mm

Width B1 of the arms 461 of the first segments 46: 0.4 mm

Length L2 of the second segments: 47: 2.0 mm

Width B2 of the second segments 47: 0.4 mm

Surface portion of bonded areas: 17.1%

Embossing depth of the first and second segments: 0.68 mm

The shearing force determined in accordance with the above-described test method of this further embodiment is 58.89 N/25 mm, wherein the material "Microplast" 42-288-HX200-PP3 by the company G. Binder GmbH & Co. KG Textil- and Kunststofftechnik, Holzgerlingen, was used again as the VELCRO fastener hook component.

The rigidity of this further nonwoven material determined in accordance with the test method disclosed in EP0699066B1 is 0.28 N, wherein, in the test arrangement, the spunbonded side is at the top, i.e. forms the surface which faces the punch of the test apparatus.

Each straight connecting line 56 between neighboring first larger areas 42 extends always through a bonded contour 44 or a bonded partial area 50 which is disposed between the first larger areas 42.

Figure 7B:
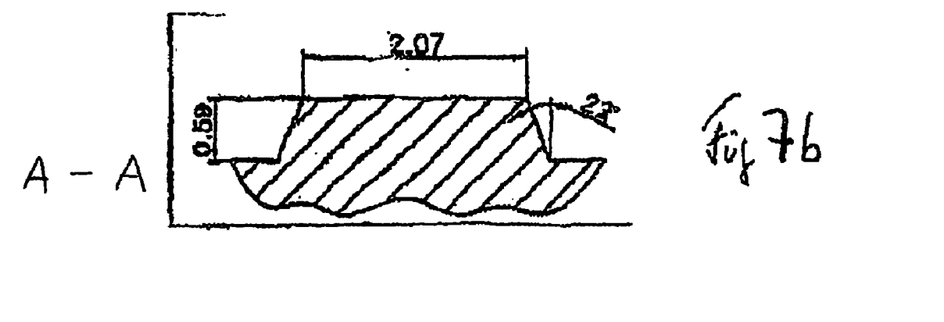

FIGS. 7a and 7b show preferred and exemplary dimensions of the embossing structure 38, wherein FIG. 7b shows a section along line A-A through a second segment 56.

Figure 8:
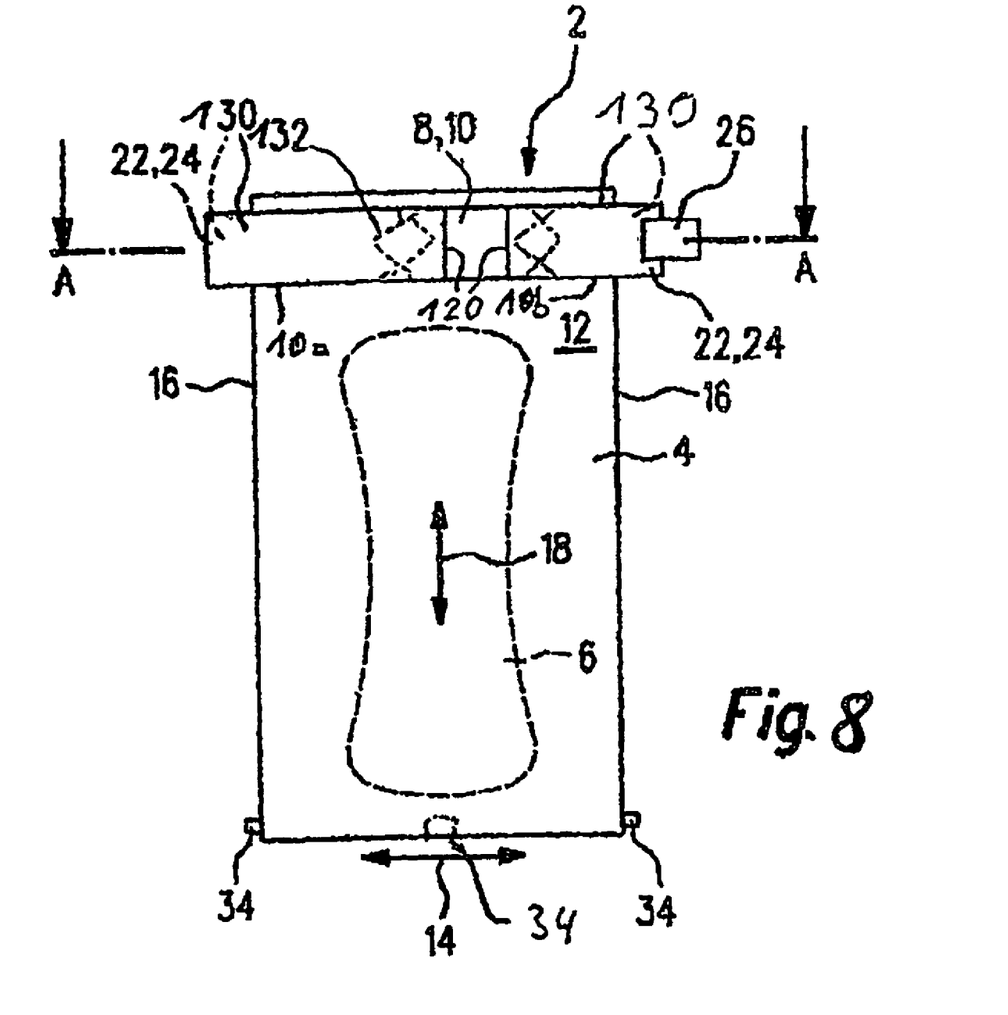
FIG. 8 shows a schematic view of an inventive belt diaper with folded hip belt.

FIG. 8 schematically shows the disposable diaper 2 with the material section 8 folded several times on top of itself about folding lines 120 on both sides of a diaper longitudinal direction 18, which form the hip belt 10. The respective free end 22 of the material section 8 forms a grasping area 24 that projects past the longitudinal side edges 16 by at least 10 mm which a user can grasp with his/her fingers. The closure element 26 is also provided at a free end 22 at this location.

The partial sections 130 of the one-piece material section 8, which are folded on top of each other, are detachably fixed to each other via a number of substantially point-shaped joining locations 132 in the form of preferably ultrasound welding points. Towards this end, a few joining locations are sufficient.

FIG. 9 is a sectional view along line A-A of FIG. 8 and shows particularly advantageous folding of the one-piece material section 8 which is mounted outside, i.e. faces away from the body, at the end of the diaper main part 4. In the present case, the diaper main part is formed at its end by a top sheet 3 on the body side and a backsheet 5 on the side of the clothes. The fold comprises four folding lines 120 on each side, each fold is thus double z-shaped. The belt is asymmetrically folded. The folding width (F1,I) of the first longer hip belt section 10$a$ is larger than the folding width (F2, I) of the shorter second hip belt section 10$b$.

The belt 10 may also be symmetrically folded, i.e. with a substantially identical folding width (F1, I; F2, I) in particular when the first and second hip belt sections (10$a$, 10$b$) have substantially the same length.

The partial sections 130 of each hip belt section 10$a$, 10$b$ which are folded on top of themselves are detachably fixed to each other by a number of substantially point-shaped joining locations 132 in the form of preferably ultrasound welding points (not shown in FIG. 9).

We claim:

1. A disposable diaper for a user or for incontinence care of a user, the diaper comprising:
a hip belt having a first hip belt section and a second hip belt section, said second hip belt section comprising a first closure element having a side facing away from the user during use and a side facing the user during use, said first hip belt section comprising a second closure element, wherein a side of said first closure element facing the user is detachably fixed to said second closure element to form a closed hip opening; and
a diaper main part having a front area, a rear area, an intermediate crotch area, and an absorptive element for liquids, wherein a longitudinal end of said front area or said rear area is detachably fixed, at a side of said hip belt facing away from the user, to a fourth closure element via at least one third mechanical closure element, wherein said third mechanical closure element is also detachably fixed to said side of said first closure element facing away from the user, wherein said hip belt is formed by a one-piece material section which is joined to said diaper main part, said one-piece material section being folded on top of itself on both sides of a longitudinal central axis about folding lines extending in a longitudinal direction of the diaper.

2. The disposable diaper of claim 1, wherein said side of said first closure element facing away from the user is at least sectionally formed by a fiber material to which said third closure element is detachably fixed.

3. The disposable diaper of claim 1, wherein said third closure element has VELCRO fastener hooks.

4. The disposable diaper of claim 1, wherein said first closure element has elastic sections.

5. The disposable diaper of claim 1, wherein said first closure element has mechanical closure elements or VELCRO fastener hooks.

6. The disposable diaper of claim 1, wherein said first closure element comprises an elastic nonwoven material to which said third closure element is fixed in a detachable manner.

7. The disposable diaper of claim 1, wherein an adhering force as shearing force between said side of said first closure element facing the user and said second closure element is at least 5 N/25 mm, at least 10 N/25 mm, at least 15 N/25 mm, at least 20 N/25 mm, at least 25 N/25 mm, at least 30 N/25 mm, at least 35 N/25 mm, at least 40 N/25 mm, at least 45 N/25 mm, or at least 50 N/25 mm, but at most 80N/25 mm.

8. The disposable diaper of claim 1, wherein an adhering force as shearing force between said side of said first closure element facing away from the user and said third closure element is at least 2 N/25 mm, at least 3.5 N/25 mm, at least 5 N/25 mm, at least 10 N/25 mm, at least 15 N/25 mm, at least 20 N/25 mm, at least 25 N/25 mm, at least 30 N/25 mm, at least 35 N/25 mm, at least 40 N/25 mm, at least 45 N/25 mm or at least 50 N/25 mm, but at most 70N/25 mm.

9. The disposable diaper of claim 1, wherein a grasping area at a free end of said hip belt, in a folded state thereof, projects in a transverse direction past a longitudinal side edge of said diaper main part by at least 10 mm, at least 20 mm, at least 30 mm, at least 40 mm, at least 50 mm or at least 60 mm.

10. The disposable diaper of claim 1, wherein, in a folded state thereof, a grasping area of said hip belt projects in a transverse direction at both free ends thereof, past a longitudinal side edge of said diaper main part.

11. The disposable diaper of claim 1, wherein a material section forming said hip belt extends, in an unfolded state, in a transverse direction past a longitudinal edge of said main part by at least 200 mm, at least 300 mm, at least 400 mm, at least 500 mm or at least 600 mm.

12. The disposable diaper of claim 1, wherein said hip belt extends in a longitudinal direction by 30 to 150 mm, 40 to 130 mm, 50 to 125 mm, 60 to 120 mm, 70 to 115 mm or 75 to 110 mm.

13. The disposable diaper of claim 1, wherein said hip belt is permanently joined to an outer side of said main part.

14. A disposable diaper for a user or for incontinence care of a user, the diaper comprising:
a hip belt having a first hip belt section and a second hip belt section, said second hip belt section comprising a first closure element having a side facing away from the user during use and a side facing the user during use, said first hip belt section comprising a second closure element, wherein a side of said first closure element facing the user is detachably fixed to said second closure element to form a closed hip opening; and
a diaper main part having a front area, a rear area, an intermediate crotch area, and an absorptive element for liquids, wherein a longitudinal end of said front area or said rear area is detachably fixed, at a side of said hip belt facing away from the user, to a fourth closure element via at least one third mechanical closure element, wherein said third mechanical closure element is also detachably fixed to said side of said first closure element facing away from the user, wherein said second closure element and/or said fourth closure element comprises a loop-forming nonwoven material as mechanical closure element, wherein a first upper side of said nonwoven material facing away from the user has first larger nonbonded areas which are separated from each other and disposed like islands, said first larger nonbonded areas being limited by bonded contours and surrounded by second smaller nonbonded areas outside of said limits and being separated from each other by said second smaller nonbonded areas, wherein said second smaller nonbonded areas surround bonded partial areas.

15. The disposable diaper of claim 14, wherein each straight connecting line between neighboring first said larger areas always extends through a bonded contour or a bonded partial area which is disposed between said first larger areas.

16. The disposable diaper of claim 14, wherein said first larger nonbonded island-type areas have a dimension or a diameter of a circle inscribed in said first area of 2 to 15 mm, 3 to 10 mm, or of 3 to 8 mm.

17. The disposable diaper of claim 14, wherein said first larger nonbonded island-type areas have a surface portion of 5 to 75° A), 5 to 60%, 10 to 50%, 10 to 45%, 15 to 45%, 20 to 40% or 30 to 40% of an overall surface of said first upper side.

18. The disposable diaper of claim 14, wherein said first larger nonbonded island-type areas are circular, oval, triangular, polygonal or hexagonal.

19. The disposable diaper of claim 14, wherein said first larger non-bonded island-type areas are separated from each other by at least 1 mm, at least 1.5 mm, at least 2 mm, at least 2.5 mm, or at least 3 mm.

20. The disposable diaper of claim 14, wherein an overall surface portion of nonbonded areas is 10 to 60%, 15 to 40%, 15 to 30%, 15 to 25%, or 19 to 22% of said first area.

21. The disposable diaper of claim 14, wherein loop-forming nonwoven material has a stiffness of at most 0.80 N, at most 0.60 N, at most 0.40 N, at most 0.30 N, at most 0.25 N, at most 0.20 N, at most 0.18 N, or at most 0.16 N, but at least 0.05 N.

22. The disposable diaper of claim 14, wherein said side of said first closure element facing away from the user is at least sectionally formed by a fiber material to which said third closure element is detachably fixed.

23. The disposable diaper of claim 14, wherein said third closure element has VELCRO fastener hooks.

24. The disposable diaper of claim 14, wherein said first closure element has elastic sections.

25. The disposable diaper of claim 14, wherein said first closure element has mechanical closure elements or VELCRO fastener hooks.

26. The disposable diaper of claim 14, wherein said first closure element comprises an elastic nonwoven material to which said third closure element is fixed in a detachable manner.

27. The disposable diaper of claim 14, wherein an adhering force as shearing force between said side of said first closure element facing the user and said second closure element is at least 5 N/25 mm, at least 10 N/25 mm, at least 15 N/25 mm, at least 20 N/25 mm, at least 25 N/25 mm, at least 30 N/25 mm, at least 35 N/25 mm, at least 40 N/25 mm, at least 45 N/25 mm, or at least 50 N/25 mm, but at most 80N/25 mm.

28. The disposable diaper of claim 14, wherein an adhering force as shearing force between said side of said first closure element facing away from the user and said third closure element is at least 2 N/25 mm, at least 3.5 N/25 mm, at least 5 N/25 mm, at least 10 N/25 mm, at least 15 N/25 mm, at least 20 N/25 mm, at least 25 N/25 mm, at least 30 N/25 mm, at least 35 N/25 mm, at least 40 N/25 mm, at least 45 N/25 mm or at least 50 N/25 mm, but at most 70N/25 mm.

29. The disposable diaper of claim 14, wherein a grasping area at a free end of said hip belt, in a folded state thereof, projects in a transverse direction past a longitudinal side edge of said diaper main part by at least 10 mm, at feast 20 mm, at least 30 mm, at least 40 mm, at least 50 mm or at least 60 mm.

30. The disposable diaper of claim 14, wherein, in a folded state thereof, a grasping area of said hip belt projects in a transverse direction at both free ends thereof, past a longitudinal side edge of said diaper main part.

31. The disposable diaper of claim 14, wherein a material section forming said hip belt extends, in an unfolded state, in a transverse direction past a longitudinal edge of said main part by at least 200 mm, at least 300 mm, at least 400 mm, at least 500 mm or at least 600 mm.

32. The disposable diaper of claim 14, wherein said hip belt extends in a longitudinal direction by 30 to 150 mm, 40 to 130 mm, 50 to 125 mm, 60 to 120 mm, 70 to 115 mm or 75 to 110 mm.

33. The disposable diaper of claim 14, wherein said hip belt is permanently joined to an outer side of said main part.

\* \* \* \* \*